US00PP36624P3

(12) United States Plant Patent
Barnes

(10) Patent No.: US PP36,624 P3
(45) Date of Patent: Apr. 22, 2025

(54) ***CALIBRACHOA* PLANT NAMED 'WNCALSBPK24'**

(50) Latin Name: ***Calibrachoa* sp.**
Varietal Denomination: WNCALSBPK24

(71) Applicant: Brent D. Barnes, Riverside, CA (US)

(72) Inventor: Brent D. Barnes, Riverside, CA (US)

(73) Assignee: WINGEN, LLC, Mustang Ridge, TX (US)

( * ) Notice: Subject to any disclaimer, the term of this patent is extended or adjusted under 35 U.S.C. 154(b) by 105 days.

(21) Appl. No.: 18/237,600

(22) Filed: Aug. 24, 2023

(65) Prior Publication Data

US 2025/0072305 P1 Feb. 27, 2025

(51) Int. Cl.
*A01H 5/02* (2018.01)
*A01H 6/82* (2018.01)

(52) U.S. Cl.
USPC ..... Plt./413
CPC ..... *A01H 6/821* (2018.05); *A01H 5/02* (2013.01)

(58) Field of Classification Search
USPC ..... Plt./413
CPC ..... A01H 6/821; A01H 5/02
See application file for complete search history.

*Primary Examiner* — Keith O. Robinson
(74) *Attorney, Agent, or Firm* — C. Anne Whealy

(57) ABSTRACT

A new and distinct *Calibrachoa* plant named 'WNCALSBPK24', characterized by its compact, upright to outwardly spreading and mounding to trailing plant habit; moderately vigorous growth habit; freely branching habit; dense and bushy appearance; early and freely flowering habit; relatively large reddish purple-colored flowers with deeper purplish red-colored centers and yellow-colored throats and excellent container and garden performance.

2 Drawing Sheets

Figure 1:
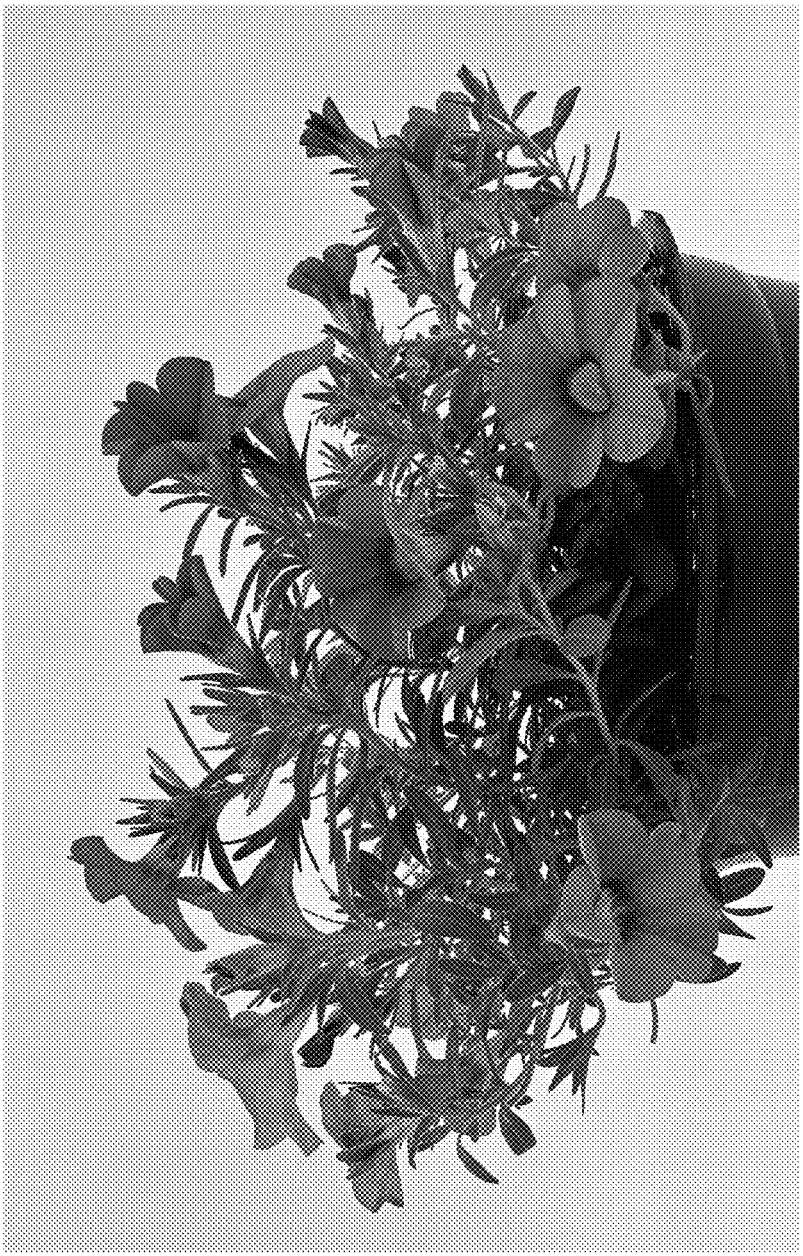

Botanical designation: *Calibrachoa* sp.
Cultivar denomination: 'WNCALSBPK24'.

BACKGROUND OF THE INVENTION

The present invention relates to a new and distinct cultivar of *Calibrachoa* plant, botanically known as *Calibrachoa* sp. and hereinafter referred to by the name 'WNCALSBPK24'.

The new *Calibrachoa* plant is a product of a planned breeding program conducted by the Inventor in Bonsall, California. The objective of the breeding program is to create new compact, uniform, freely-branching and freely-flowering *Calibrachoa* plants with unique and attractive flowers and good container and garden performance.

The new *Calibrachoa* plant originated from a cross-pollination conducted by the Inventor in Bonsall, California on Sep. 25, 2019 of a proprietary seedling selection of *Calibrachoa* sp. identified as code number 18CB273-01, not patented, as the female, or seed, parent with *Calibrachoa* sp. 'Duecalhulblu', disclosed in U.S. Plant Pat. No. 30,202, as the male, or pollen, parent. The new *Calibrachoa* plant was discovered and first selected by the Inventor as a single flowering plant within the progeny of the stated cross-pollination in a controlled greenhouse environment in Bonsall, California on Jun. 1, 2020.

Asexual reproduction of the new *Calibrachoa* plant by vegetative terminal cuttings in a controlled greenhouse environment in Bonsall, California since Jun. 3, 2020 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNCALSBPK24'. These characteristics in combination distinguish 'WNCALSBPK24' as a new and distinct *Calibrachoa* plant:

1. Compact, upright to outwardly spreading and mounding to trailing plant habit.
2. Moderately vigorous growth habit.
3. Freely branching habit; dense and bushy appearance.
4. Early and freely flowering habit.
5. Relatively large reddish purple-colored flowers with deeper purplish red-colored centers and yellow-colored throats.
6. Excellent container and garden performance.

Plants of the new *Calibrachoa* differ primarily from plants of the female parent selection in the following characteristics:

1. Plants of the new *Calibrachoa* are more trailing than and not as spreading as plants of the female parent selection.
2. Plants of the new *Calibrachoa* are smaller than and not as vigorous as plants of the female parent selection.
3. Flowers of plants of the new *Calibrachoa* are lighter in color than flowers of plants of the female parent selection.

Plants of the new *Calibrachoa* differ primarily from plants of the male parent, 'Duecalhulblu', in flower color as flowers of plants of the new *Calibrachoa* are reddish purple in color with deeper purplish red-colored centers and yellow-colored throats whereas flowers of plants of 'Duecalhul-blu' are light and dark purple in color with light yellow-colored throats.

Plants of the new *Calibrachoa* can be compared to plants of the *Calibrachoa* sp. 'USCALI11', disclosed in U.S. Plant Pat. No. 14,968. In side-by-side comparisons, plants of the new *Calibrachoa* differ primarily from plants of 'USCALI11' in the following characteristics:

1. Plants of the new *Calibrachoa* are more compact and denser than and not as open as plants of 'USCALI11'.
2. Plants of the new *Calibrachoa* are not as vigorous as plants of 'USCALI11'.
3. Plants of the new *Calibrachoa* flower earlier than plants of 'USCALI11'.
4. Flowers of plants of the new *Calibrachoa* are flatter and more open than flowers of plants of 'USCALI11'.
5. Flowers of plants of the new *Calibrachoa* are slightly lighter in color than flowers of plants of 'USCALI11'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1) is a side perspective view of a typical flowering plant of 'WNCALSBPK24' grown in a container.

Figure 2:
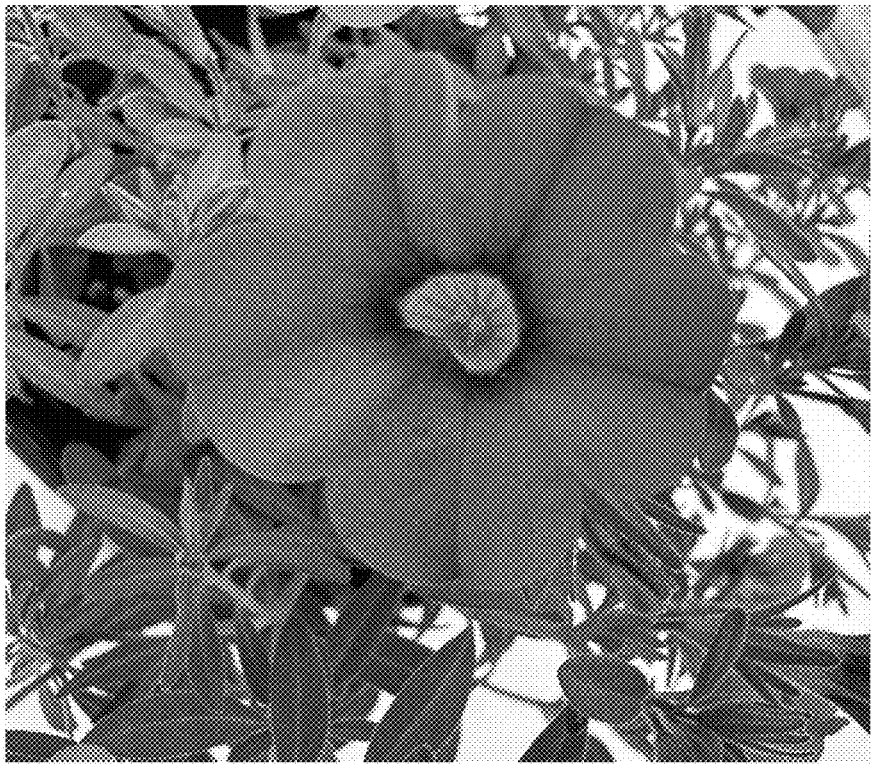

The photograph on the second sheet (FIG. 2) is a close-up view of a typical flowering plant of 'WNCALSBPK24'.

DETAILED BOTANICAL DESCRIPTION

The aforementioned photographs and following observations and measurements describe plants grown during the spring in 723-ml containers in a glass-covered greenhouse in Loudon, New Hampshire and under cultural practices typical of commercial *Calibrachoa* production. During the production of the plants, day and night temperatures averaged 20° C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Calibrachoa* sp. 'WNCALSBPK24'.

Parentage:

*Female, or seed, parent.*—Proprietary seedling selection of *Calibrachoa* sp. identified as code number 18CB273-01, not patented.

*Male, or pollen, parent.*—*Calibrachoa* sp. 'Duecalhul-blu', disclosed in U.S. Plant Pat. No. 30,202.

Propagation:

*Type.*—By vegetative terminal cuttings.

*Time to initiate roots, summer.*—About five to seven days at ambient temperatures about 28° C.

*Time to initiate roots, winter.*—About seven to ten days at ambient temperatures about 20° C.

*Time to produce a rooted plant, summer.*—About four to five weeks at ambient temperatures about 28° C.

*Time to produce a rooted plant, winter.*—About five to six weeks at ambient temperatures about 20° C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright to outwardly spreading and mounding to eventually trailing plant habit; freely branching habit with about eight to twelve primary lateral branches with secondary laterals developing potentially at every node, dense and bushy plant form; pinching enhances development of lateral branches; moderately vigorous growth habit and rapid growth rate.

*Plant height.*—About 14 cm.

*Plant diameter.*—About 27 cm by 29 cm.

Lateral branch description:

*Length.*—About 14 cm.

*Diameter.*—About 2 mm.

*Internode length.*—About 1.1 cm.

*Strength.*—Moderately strong, flexible and sturdy.

*Aspect.*—About 30 to 70 degrees from stem axis.

*Texture and luster.*—Densely pubescent; pubescence, minute; matte to slightly glossy.

*Color, developing.*—Close to 144A.

*Color, developed.*—Close to 144A.

Leaf description:

*Arrangement.*—Alternate, simple.

*Length.*—About 2.3 cm to 2.6 cm.

*Width.*—About 7 mm.

*Shape.*—Narrowly elliptic.

*Apex.*—Broadly acute to rounded.

*Base.*—Attenuate.

*Margin.*—Entire.

*Texture and luster, upper and lower surfaces.*—Sparsely to moderately pubescent; pubescence, minute; matte to slightly glossy.

*Venation pattern.*—Pinnate; arcuate.

*Color.*—Developing leaves, upper surface: Close to 147A. Developing leaves, lower surface: Close to 146A. Fully expanded leaves, upper surface: Close to between NN137A and 147A; midvein, close to 146A and lateral venation, close to between NN137A and 147A. Fully expanded leaves, lower surface: Close to 147A; midvein, close to 146A and lateral venation, close to 147A.

*Petioles.*—Length: About 5 mm. Diameter: About 2 mm. Strength: Moderately strong, flexible. Texture and luster, upper and lower surfaces: Sparsely pubescent; pubescence, minute; matte to slightly glossy. Color, upper and lower surfaces: Close to 146A.

Flower description:

*Flower type and flowering habit.*—Single salverform flowers arising from leaf axils; freely flowering habit with typically about 55 to 70 flowers and flower buds developing per plant at one time; flowers face upright to outwardly to slightly nodding.

*Fragrance.*—None detected.

*Natural flowering season.*—Plants of the new *Calibrachoa* begin flowering about five weeks after planting; plants flower continuously from the spring though the summer until frost.

*Flower longevity.*—Depending on temperature, about one to two weeks; flowers persistent.

*Flower buds, before showing petal color.*—Length: About 1 cm. Diameter: About 3 mm. Shape: Oblong, elongate. Texture and luster: Sparsely to moderately pubescent; pubescence, minute; matte. Color: Close to 146A.

*Flower diameter.*—About 3.5 cm by 3.6 cm.

*Flower length (height).*—About 2.4 cm.

*Flower throat diameter.*—About 7 mm by 8 mm.

*Flower tube length.*—About 1.5 cm.

*Flower tube diameter, proximally.*—About 2.5 mm to 3 mm.

*Corolla.*—Arrangement: Five fused petals opening into a flared trumpet. Petal lobe length (from throat): About 1.4 cm to 1.6 cm. Petal lobe width: About 1.5 cm to 1.6 cm. Petal shape: Fan-shaped with slight cordate tendencies. Petal apex: Broadly rounded to shallowly retuse; slightly recurving with development. Petal margin: Entire; slightly undulate. Petal texture and luster, upper surface: Smooth, glabrous; velvety; matte. Petal texture and luster, lower surface: Smooth, glabrous; slightly glossy. Throat texture and luster: Smooth, glabrous; slightly glossy. Tube texture and luster: Moderately pubescent; slightly glossy. Color: Petal lobe, when opening, upper surface: Closest to 72A. Petal lobe, when opening, lower surface: Closest to N75A. Petal lobe, fully opened, upper surface: Closest to 72A to 72B; towards the throat, close to 71A; primary venation, close to 71A, and lateral venation, close to 144A tinged with close to 72A; colors do not change with subsequent development. Petal lobe, fully opened, lower surface: Closest to N75A to N75B; venation, close to 144A; colors do not change with subsequent development. Throat: Close to 6A; venation, close to 6A. Tube: Close to 154D; venation, close to 144A and 154D.

*Calyx.*—Arrangement: One star-shaped calyx tube with five sepals fused towards the base and arranged in a single whorl; sepals flaring outwardly and reflexing towards the apex. Length: About 1.8 cm. Diameter: About 2.2 cm. Sepal length: About 1.8 cm. Sepal width: About 4 mm. Sepal shape: Narrowly lanceolate. Sepal apex: Acute. Sepal margin: Entire. Sepal texture and luster, upper and lower surfaces: Moderately pubescent; pubescence, minute; matte. Sepal color, upper surface: More green than 146A. Sepal color, lower surface: Close to 146A.

*Peduncles.*—Length: About 1.5 cm to 1.75 cm. Diameter: About 1.25 mm. Angle: About 30 to 45 degrees from stem axis. Strength: Moderately strong, wiry and flexible. Texture and luster: Moderately pubescent; pubescence, minute; matte to slightly glossy. Color: Close to 146A.

*Reproductive organs.*—Stamens: Quantity: Five per flower. Filament length: About 9 mm. Filament color: Close to 145D. Anther size: About 1 mm by 1 mm. Anther shape: Round to slightly oblong. Anther color: Close to 6A. Pollen amount: If observed, scarce. Pollen color: Close to 6A. Pistils: Quantity: One per flower. Pistil length: About 1 cm. Style length: About 8 mm. Style color: Close to 145A. Stigma diameter: About 1 mm. Stigma shape: Round. Stigma color: Close to 144A. Ovary color: Close to 144A.

*Seeds and fruits.*—To date, seed and fruit development have not been observed on plants of the new *Calibrachoa.*

Garden performance: Plants of the new Petunia have been observed to have excellent garden performance and have been observed to tolerate rain, wind and temperatures ranging from about 1° C. to about 35° C.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'WNCALSBPK24' as herein illustrated and described.

* * * * *